ROSE PLANT
Filed Jan. 6, 1970 2 Sheets-Sheet 1
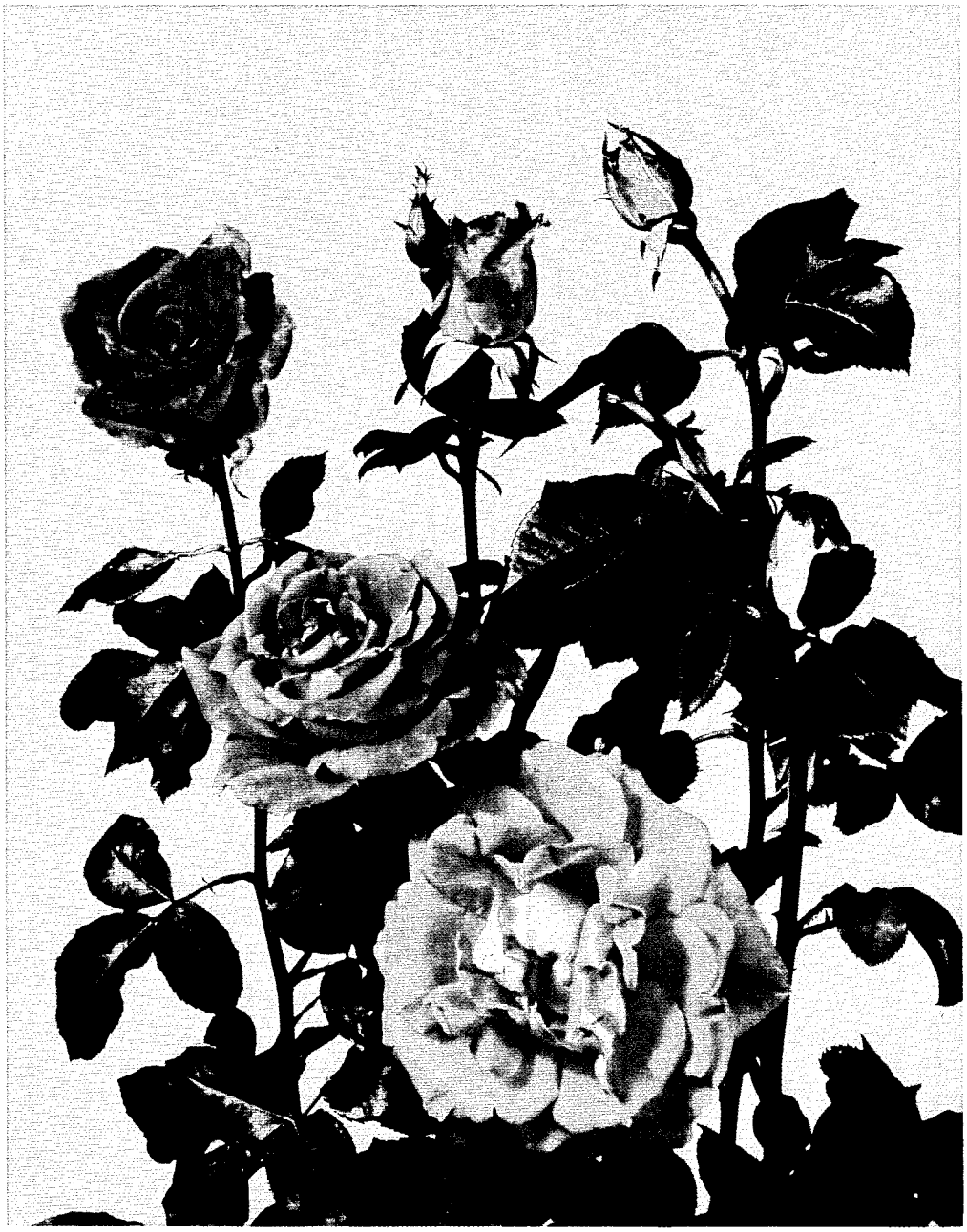

ROSE PLANT
Filed Jan. 6, 1970 2 Sheets-Sheet 2
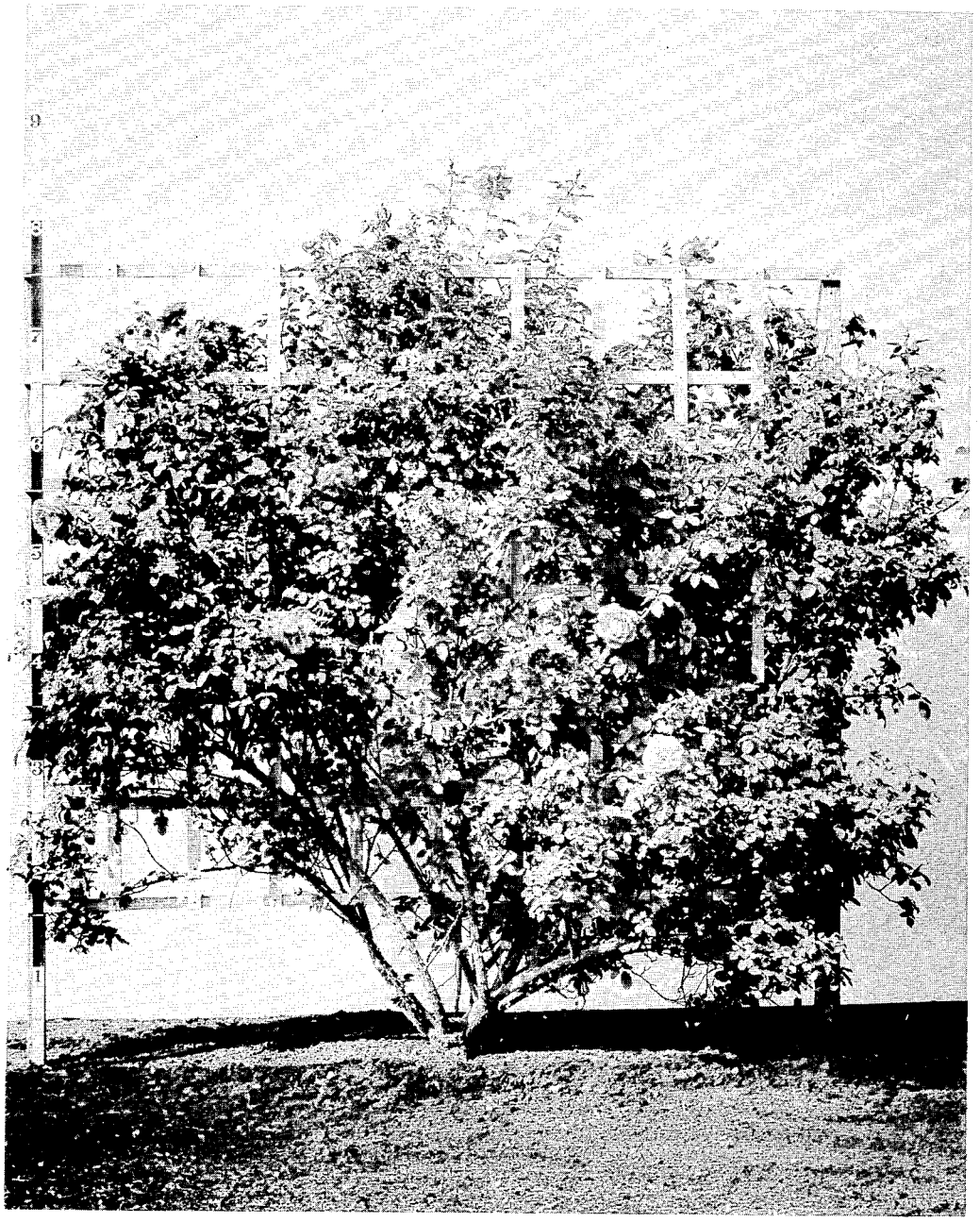

United States Patent Office

Plant Pat. 3,076
Patented Oct. 19, 1971

3,076

ROSE PLANT

David L. Armstrong, Upland, Calif., assignor to
Armstrong Nurseries, Inc., Ontario, Calif.

Filed Jan. 6, 1970, Ser. No. 1,066
Int. Cl. A01h 5/00
U.S. Cl. Plt.—2 1 Claim

ABSTRACT OF THE DISCLOSURE

A climbing rose plant of the hybrid tea class, which is tall growing and has semi-glossy leaves of leathery texture, comprising three to seven leaflets of medium to large size; the flowers of said plant having a subdued fragrance and being of quite large size. The double petals are arranged regularly when fully open. The flowers are borne usually singly, but sometimes three or four, or even more, appear in irregular clusters on strong medium to long stems. The plant is free blooming outdoors, and blooms nearly continuously during the growing season. Its habit of growth is notably vigorous, tall, upright and branching.

This invention relates to a new variety of climber rose plant of the hybrid tea class. The plant is tall-growing in habit and is well adapted to outdoor cultivation both for cut flowers, and for garden decoration.

The plant, a seedling bred by crossing Buccaneer (P.P. No. 1,119) as the seed parent with Bravo (P.P. No. 983) as the pollen parent, holds its distinguishing characteristics through successive propagations by budding. It was originally propagated in Ontario, Calif.

The new variety is distinguished from its seed parent, Buccaneer, in the following respects: Whereas, Bucaneer is a grandiflora rose, the present variety is a climbing hybrid tea rose; whereas the flowers of Buccaneer are popularly described as buttercup yellow in color, the flowers of the new variety are purplish red. Whereas Buccaneer flowers are relatively small in size, the flowers of the present variety are about 2" larger. Whereas Buccaneer flowers are cupped in form, the new variety is high-centered when open, giving an exceptionally good formal effect. Whereas Buccaneer is moderately fragrant, the fragrance of the new variety is relatively quite subdued.

The new variety is distinguished from its pollen parent, Bravo, in the following ways: Whereas Bravo is a bush rose of the hybrid tea class, this new variety has a climbing habit of growth. Whereas the flower of the Bravo rose is popularly described as cardinal red in color, the flower of this new variety is lighter purplish red. Both flowers are double, but Bravo has more than 35 petals, whereas the new variety has fewer, usually from 25 to 30. The flowers of Bravo usually range from 4" to 5", whereas the new variety is somewhat larger, often 5½". Whereas the Bravo rose sets very little seed outdoors under normal garden conditions, this new variety sets seed very readily by natural means when raised in Ontario, Calif.

FIG. 1 of the accompanying drawings shows the flowering of the plant in color, from bud to full bloom. FIG. 2 shows the plant in black and white, illustrating its extremely vigorous growth habit.

The flowers of the new variety, as observed in Ontario, Calif., are usually borne singly, on strong medium to long stems, but sometimes appear in irregular clusters of three or four. The plant blooms freely outdoors and almost continuously during the growing season. The fragrance is slight to moderate.

In the description which follows, the color values stated conform to the Nickerson Color Fan.

*Bud*

As to the bud: the peduncle is of average length, of average caliper, and erect. The peduncle may have several to many stipitate glands, and may have a few small prickles, or none at all. Its color is near to Strong Yellow Green, 5GY6/8, overlaid with near Moderate Yellowish Brown, 10YR4/4 on the side exposed to the sun.

Before the calyx breaks, the bud is of medium size, short to medium length, and of ovoid form, with foliaceous appendages and some glandular bloom on the surface of the bud, the foliaceous parts extending beyond the tip of the bud for a distance equal to about one-half of its length, or slightly more.

As the calyx breaks, the color is between Strong Red, 5R4/12, and Moderate Red, 2.5R4/10. A fine, wooly tomentum covers the inner surface of the sepals, and lines the margins of alternate sepals; margins of other sepals have from few to several small stipitate glands and small slender foliaceous parts. The sepals sometimes have foliaceous appendages extending for a distance equal to from one-fourth to one-third of the length of the sepal. The outside surface of the sepals is usually provided with from a few to several small stipitate glands.

As the first petal opens, the bud will be of average size, medium length, and ovoid form, usually progressing to urn-shaped. The color outside will approach Strong Purplish Red, 7.5RP5/12, in the upper area, blending with near Strong Yellowish Pink, 5R7/9, toward the base of the petal; the small area at the base of the petal will be near Vivid Yellow, 5Y8/12. The inside color will be near Strong Purplish Red, 10RP4/12, blending with near Deep Yellowish Pink, 5R6/11, toward the base of the petal. The small area at the base of the petal will be near Greenish Yellow, 7.5Y8/12. The bud opens up well and it is not retarded or prevented from opening by cold, hot dry, or wet weather.

*Bloom*

The bloom when fully open is of large size, usually from 5 to 5½" in diameter. The petalage is double, and the bloom comprises from 25 to 30 petals, plus 5 to 10 petaloids, in regular arrangement. Its form is high-centered at first, later becoming flat or slightly cupped. The petals at first are tightly cupped, with the tips rolled outward. At maturity, they are somewhat less tightly rolled.

*Petals*

The petals are medium thick in texture, and moderately leathery, with a satiny surface both inside and outside. The outside petals are between round and broadly obovate in form, with apex flat, and usually with 2 to 3 notches. The intermediate petals are broadly obovate, with apex rounded, sometimes with 1 or 2 notches. The inside petals are likewise broadly obovate. The colors may be modified by being shaded and/or washed with other colors.

The following description is of the newly opened flower of a rose grown outdoors in the month of October, in Ontario, Calif.:

The outer surface of the outside petal is near Deep Purplish Pink, 7.5RP6/12, blending with near Deep Pink, 2.5R6/11. The small area towards the base of the petal is near Vivid Greenish Yellow, 7.5Y8/12. The inside surface of the outside petal is near Strong Purplish Red, 10RP4/12, blending with near Deep Yellowish Pink, 5R6/11, toward the base of the petal. The small area at the base of the petal is near Vivid Yellow 5Y8/12.

The outer surface of the intermediate petal is near Moderate Pink, 5R8/6, blending with near Light Orange, 5YR8/7, toward the base of the petal. The small area towards the base of the petal is near Vivid Yellow, 5Y8/12. The inside surface of the intermediate petal is near Strong Purplish Red, 10RP5/12, blending with near Deep Yellowish Pink, 5R6/11, toward the base of the petal. The small area towards the base of the petal is near Vivid Yellow, 5Y8/12.

The outer surface of the inner petal is near Moderate Yellowish Pink, 10R8/6, blending with near Moderate Orange Yellow, 7.5YR8/8 toward the base of the petal. The small area towards the base of the petal is near Vivid Yellow, 5Y8/12. The inside surface of the inner petal is near Strong Red, 2.5R5/12, blending with near Strong Reddish Orange, 7.5R6/12, toward the base of the petal. The small area towards the base of the petal is near Vivid Yellow, 5Y8/12.

The following description is of a flower of the new variety that has been open for three days outdoors in the month of October in Ontario, Calif.:

The outer surface of the outside petal is near Deep Purplish Pink, 7.5RP6/12. The small area towards the base of the petal is near Brilliant Yellow, 5Y9/9. The inside surface of the outside petal is between Strong Purplish Red, 7.5RP5/12, and Deep Purplish Pink, 7.5RP6/12. The small area towards the base of the petal is near Vivid Greenish Yellow, 7.5Y8/12.

The outer surface of the inside is near Moderate Pink, 2.5R8/5, blending with near Light Yellowish Pink, 2.5YR9/3 toward the base of the petal. The small area towards the base of the petal is near Brilliant Greenish Yellow, 7.5Y9/8. The inside surface of the inside petal is near Strong Purplish Red, 10RP5/12, blending with near Deep Pink, 2.5R6/11, toward the base of the petal.

The general color effect of the bloom as a whole lies between Strong Purplish Red, 10RP5/12, and Strong Purplish Red, 10RP4/12, when the flower is newly open. Three days later, the general effect will lie between Strong Purplish Red, 7.5RP5/12, and Strong Purplish Red, 10RP5/12.

The petals drop off cleanly. They are not particularly affected by cold, hot, wet, or dry weather.

Flowers on plants in the garden will last from three to four days in the month of November, in Ontario, Calif. Cut roses grown outdoors and kept at livingroom temperatures will last from two to three days in the same locale and during November.

*Reproductive organs*

Stamens: From average number to many, arranged regularly about the pistils, a few mixed with petaloids.

Filaments: Medium length to long, 5 to 20 mm. Color: near Vivid Yellow, 5Y8/12. Most with anthers.

Anthers: Medium to large, all open approximately at once. Both on the upper side and on the under side, the margins of the anthers are near Strong Orange Yellow, 7.5YR7/11, with the remaining surface near Brilliant Yellow, 5Y9/9.

Pollen: Moderately abundant, near Strong Orange Yellow, 7.5YR7/11, in color.

Pistils: About the average number—approximately 75.

Styles: Uneven, short to average length, thin and bunched. The upper third of the style is near Strong Red, 5R4/12; the remainder near Brilliant Greenish Yellow, 7.5Y9/8.

Stigma: Near Brilliant Greenish Yellow, 7.5Y9/8, in color.

Ovaries: All usually enclosed in the calyx.

Hips: Short, globular. Near Strong Orange, 5YR6/11, in color when mature. They are smooth, with thick, fleshy walls.

Sepals: Falling soon; medium length and straight.

Seeds: Medium to large size, and from 8 to 12 in number.

*Foliage*

The leaves are compound, usually comprising from 3 to 7 leaflets. They are abundant and of medium to large size, semi-glossy and leathery in texture. The leaflets are oval with apex acute, round base, and margin simply serrate.

The upper surface of the mature leaf is between Grayish Olive Green, 5GY3/2, and Moderate Olive Green, 7.5GY4/4. The under surface of the mature leaf is between Moderate Yellow Green, 5GY5/6, and Moderate Yellow Green, 7.5GY5/7.

The young leaf displays an upper surface which is between Moderate Olive Green, 7.5GY4/4, and Moderate Olive Green, 5GY4/3. The under surface of the young leaf is near Moderate Yellow Green, 2.5GY5/5.

Rachis: The leaf stem is heavy and its upper side is grooved, with few, if any, stipitate glands on its edges. On the underside, the rachis is smooth, but sometimes with one or two small prickles.

Stipules: Medium length, narrow, with short points turning out at an angle of more than 45°.

Disease resistance: The plant has more than average resistance to mildew, in comparison with other varieties now in commerce, under comparable conditions in Ontario, Calif.

*Growth*

The plant is of climbing habit, much branched. It displays vigorous growth, producing heavy canes. The main stems are near Moderate Yellow Green, 2.5GY5/5, and they carry several large prickles of medium length which are almost straight and which have short, narrow bases. The prickles are between Strong Brown, 5YR4/5, and Strong Yellowish Brown, 7.5YR5/7. There are few, if any, small prickles, and such as there are are of the same color as the large prickles.

Branches: The branches are between Moderate Yellow Green, 5GY5/6, and Moderate Yellow Green, 7.5GY5/7. They carry several large prickles of medium length which are hooked slightly downward and have short, narrow bases. Their color is between Strong Brown, 5YR4/5, and Moderate Brown, 7.5YR4/5. There are few, if any, small prickles, and such as there are are of the same color as the large prickles. There are no hairs either on the branches or on the main stems.

New shoots: Between Moderate Yellow Green, 5GY5/6, and Strong Yellow Green, 5GY6/8, overlaid with near Moderate Reddish Brown, 2.5YR3/3, on the side exposed to the sun. The large prickles on the new shoots are few in number, of medium length, hooked downward, with medium length narrow bases. In color they are near Moderate Reddish Brown, 2.5YR3/3. There are no small prickles and no hairs on the new shoots.

I claim:

1. A rose plant of the hybrid tea class, substantially as shown and described, which is distinguished by a novel combination of features including: vigorous growth and climbing habit of the plant; its tendency to flower heavily during blooming cycles and to repeat blooming cycles throughout the season; the strong purplish red color of its relatively large sized blooms with regularly placed petaloids and double petalage, carried usually on strong single stems, but sometimes clustered.

No references cited.

ROBERT E. BAGWILL, Primary Examiner